(12) United States Patent
Mantelle et al.

(10) Patent No.: US 6,348,211 B1
(45) Date of Patent: *Feb. 19, 2002

(54) COMPOSITIONS AND METHODS FOR TREATMENT OF ATTENTION DEFICIT DISORDER AND ATTENTION DEFICIT/HYPERACTIVITY DISORDER WITH METHYLPHENIDATE

(75) Inventors: Juan Mantelle; Terese A. Dixon, both of Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/618,626

(22) Filed: Jul. 18, 2000

Related U.S. Application Data

(63) Continuation of application No. 09/161,351, filed on Sep. 30, 1998, now Pat. No. 6,149,374.
(60) Provisional application No. 60/069,510, filed on Dec. 15, 1997.
(51) Int. Cl.⁷ .................................................. A61F 13/02
(52) U.S. Cl. ...................................... 424/448; 424/449
(58) Field of Search .................................. 424/448, 449

(56) References Cited

U.S. PATENT DOCUMENTS

| | | |
|---|---|---|
| 2,957,880 A | 10/1960 | Rometsch |
| 4,310,509 A | 1/1982 | Berglund et al. |
| 5,474,783 A | 12/1995 | Miranda et al. |
| 5,601,839 A | 2/1997 | Quan et al. |
| RE35,474 E | 3/1997 | Woodard et al. |
| 5,614,178 A | 3/1997 | Bloom et al. |
| 5,629,019 A | 5/1997 | Lee et al. |
| 5,665,286 A | 9/1997 | Miranda et al. |
| 5,780,050 A | 7/1998 | Jain et al. |

FOREIGN PATENT DOCUMENTS

| | | |
|---|---|---|
| EP | 0 881 216 A1 | 12/1998 |
| WO | 98/39042 | 11/1998 |

OTHER PUBLICATIONS

Patrick (1989.) "The absorption of sustained–released methylphenidate formulations compared to an immediate–release formulation." *Biopharmaceutics & Drug Disposition* 10: 165–171.

Gualtieri et al., (1989) "Clinical Studies of Methylphenidate Serum Levels in Children and Adults." *Journal of the American Academy of Child Psychiatry*, 21: 19–26.

Primary Examiner—S. Mark Clardy
Assistant Examiner—Michael A. Williamson
(74) Attorney, Agent, or Firm—Foley & Lardner

(57) ABSTRACT

The invention relates to a method of treating Attention Deficit Disorder (ADD) and Attention Deficit/Hyperactivity Disorder (ADHD) and compositions for topical application of methylphenidate comprising methylphenidate in a flexible, finite system wherein the methylphenidate is present in an amount sufficient to achieve substantially zero order kinetics for delivery to the skin or mucosa of a patient in need thereof over a period of time at least 10 hours.

31 Claims, 3 Drawing Sheets

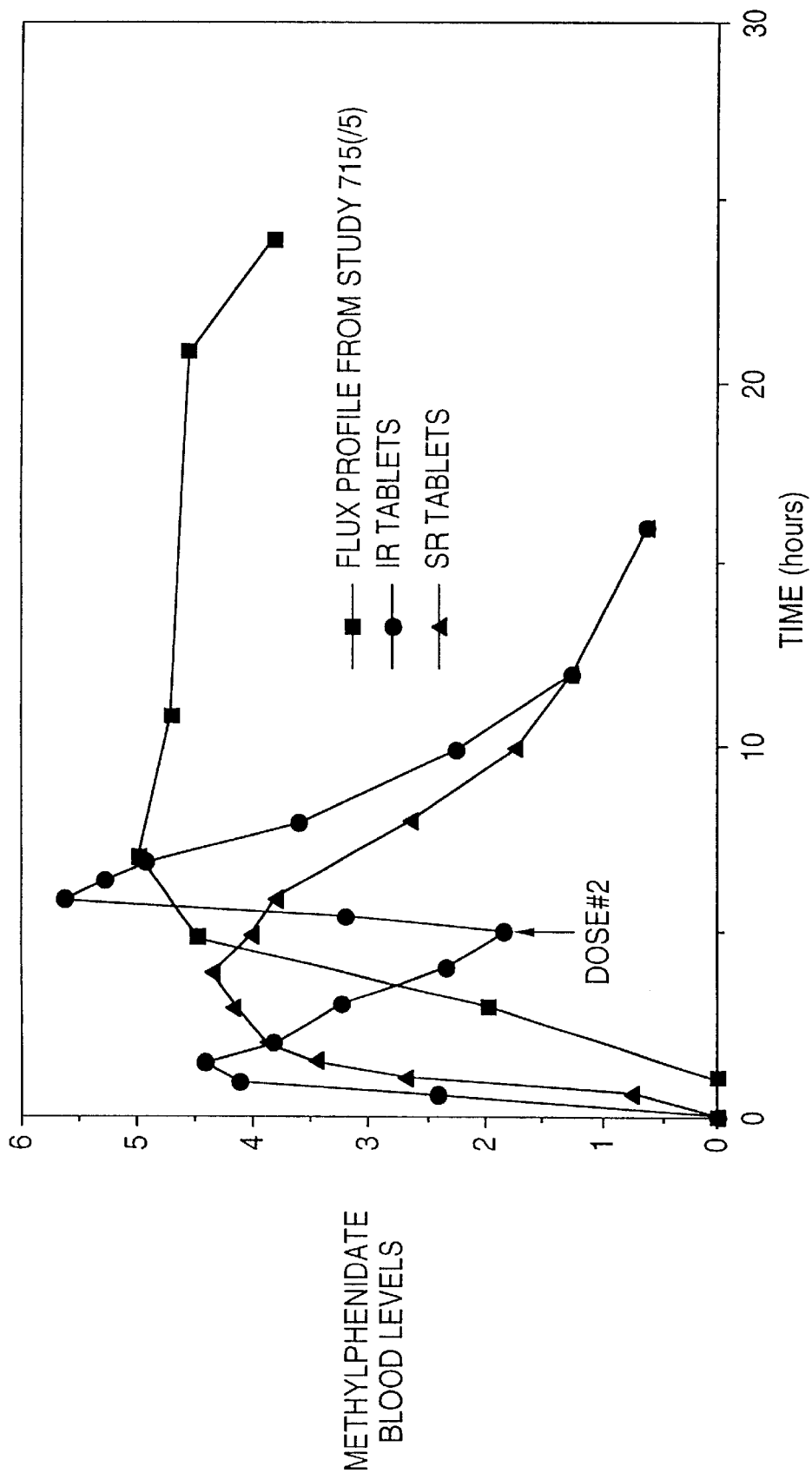

COMPOSITIONS AND METHODS FOR TREATMENT OF ATTENTION DEFICIT DISORDER AND ATTENTION DEFICIT/ HYPERACTIVITY DISORDER WITH METHYLPHENIDATE

The present application is a continuation of U.S. patent application Ser. No. 09/161,351, filed Sep. 30, 1998, now U.S. Pat. No. 6,149,374, which claims the benefit of U.S. provisional application No. 60/069,510, filed Dec. 15, 1997.

FIELD OF THE INVENTION

The present invention relates to compositions and methods of treatment of Attention Deficit Disorder (ADD) and Attention Deficit/Hyperactivity Disorder (ADHD) by means of topical application of methylphenidate in a pharmaceutically acceptable adhesive carrier, in an amount sufficient to achieve substantially zero-order kinetics over a period of at least 10 hours.

BACKGROUND OF THE INVENTION

Attention Deficit Disorder (ADD) and Attention Deficit/ Hyperactivity Disorder (ADHD) (severally and collectively hereinafter referred to as "AD") are developmental disorders of self-control. They consist of problems with attention span, impulse control and activity level. These problems are reflected in impairment of a person's will or capacity to control his or her own behavior relative to the passage of time and to keep future goals and consequences in mind.

Traditionally, methylphenidate has been used as the drug of choice for the treatment of AD in both children and adults for several reasons. Methylphenidate, described in U.S. Pat. No. 2,957,880, is a central nervous system stimulant. Though not an amphetamine, methylphenidate functions in a similar way in the brain. The current commercially available dosage form (Ritalin® tablets) and available strengths of the tablets fall short of providing effective treatment for a significant portion of the patient's waking hours. Methylphenidate has a short duration of action of from about 2 to 4 hours. A controlled release tablet of methylphenidate is commercially available, but is available only in one strength. This product, which was designed to eliminate the need for multiple administration of a tablet during the school day for children and reduce dosing to either once or twice a day, falls short of providing effective treatment for a significant portion of the patient's waking hours.

The regimen of methylphenidate currently used for ADHD exhibits numerous shortcomings that include fluctuations in blood levels with immediate release tablets; inconvenience of successfully complying with more frequent dosing (for examples, inability of children to accurately monitor time and/or stigma of medication); difficulty for young children to swallow tablets whole; availability of only two types of tablets available, immediate release tablets and sustained release tablets, ineffectiveness of BID (behavioral inhibition disorder) dosing for a significant portion of the patient's waking hours; and potential for drug abuse.

Topical application of drugs provides many advantages over conventional oral administration. Advantages include convenience, uninterrupted therapy, improved patient compliance, ease of discontinuance, elimination of hepatic first pass metabolism, a high degree of control over blood concentration of the drug and improved overall therapy.

The term "topical" or "topically" is used herein in its conventional meaning as referring to direct contact with a spot on a mammal, which can be any anatomical site or surface area including skin or mucous membranes, or hardened tissue such as teeth or nails.

The term "application" is intended to mean any mode which results in systemic administration.

The term "mucosa" or "mucosal" as used herein means oral, buccal, vaginal, rectal, nasal, intestinal, and ophthalmic surfaces.

Although topical application systems have many advantages, most drugs do not readily lend themselves to this mode of administration due to the well known barrier properties of the skin. Molecules moving from the environment into and through intact skin must first penetrate the stratum corneum, the outer horny layer of the skin, and any material on its surface. The molecule must then penetrate the viable epidermis and the papillary dermis before passing through the capillary walls and into the systemic circulation. Along the way, each of the above-mentioned tissues will exhibit a different resistance to penetration by the same molecule. However, it is the stratum corneum, a complex structure of compact keratinized cell remnants separated by extracellular lipid domains, that presents the greatest barrier to absorption of topical compositions or transdermally administered drugs.

There are topical application systems known in the art which provide a means for transdermal delivery of various drugs where methylphenidate is mentioned, e.g., in Quan et al., U.S. Pat. No. 5,601,839, a transdermal delivery system is disclosed. A basic drug having a pKa of 8.0 or greater is incorporated into the delivery system. The formulation also requires the use of triacetin as a permeation enhancer. Quan et al. lists oxybutynin, scopolamine, fluoxetine, epinephrine, morphine, hydromorphone, atropine, cocaine, buprenorphine, chlorpromazine, imipramine, desipramine, methylphenidate, methamphetamine, lidocaine, procaine, pindolol, nadolol, and carisoprodol as preferred "basic drugs." Bloom et al., U.S. Pat. No. 5,614,178, discloses a composition for topical delivery comprising an effective amount of a pharmaceutically active substance, a high molecular weight crosslinked cationic polymer, a non-ionic surfactant, an alkoxylated ether and a pharmaceutically acceptable carrier. Bloom et al. includes a myriad of different drugs for incorporation into the topical delivery system. Lee et al., U.S. Pat. No. 5,629,019 discloses a transdermal delivery composition containing a hydrophobic permeation enhancer, which permeation enhancer has been micronized and stabilized in an inert carrier. These compositions can include a biologically active substance to provide enhanced permeability of the active agent to the skin or mucosa. Lee et al. lists over 100 beneficial agents to be included in the transdermal delivery composition.

Therefore, despite the existence of many different types of topical application systems in the art, there remains a continuing need for improving the method of delivery of methylphenidate to a patient. Accordingly, a new topical application system whereby delivery of the active substance, herein methylphenidate, achieves substantially zero-order kinetics over a time period of at least 10 hours has been developed.

SUMMARY OF THE INVENTION

It is therefore an object of the present invention to provide a composition for topical application of methylphenidate. The foregoing objects are achieved by providing methylphenidate in a pharmaceutically acceptable topical carrier, in an amount sufficient to achieve substantially zero order kinetics for at least 10 hours to the skin or mucosa of a patient in need thereof.

The foregoing objects are also achieved by providing a composition for topical application of methylphenidate comprising methylphenidate in a flexible, finite system wherein the methylphenidate is present in an amount sufficient to permit a delivery rate from about 0.5 mg/24 hours to about 100 mg/24 hours in order to achieve a therapeutically effective dose in a patient.

In a preferred embodiment, the carrier comprises an adhesive. It is another object of the present invention is to provide the methylphenidate of the above described composition in the form of a base or a base/basic salt combination, or an ester form.

In another embodiment of the invention, the preparation in the carrier delivers about at least 0.5 mg per 24 hours, preferably in a preparation that contains about at least 26.4 mg of methylphenidate base per about 10 cm$^2$.

In another embodiment of the invention, the composition further comprises an enhancer.

Yet another object of the present invention is to treat attention deficit/hyperactivity disorder in a child or adult by applying a transdermal delivery system comprising methylphenidate in an amount effective to achieve zero-order kinetics as described above.

The foregoing and other objects of the invention are also achieved by the present invention which is directed to a topical application system for delivery of methylphenidate wherein the methylphenidate is administered in an amount effective to achieve zero-order kinetics during the patient's waking hours.

Further objects, features and advantages of the present invention will be apparent from consideration of the detailed description of preferred embodiments which follow.

BRIEF DESCRIPTION OF THE DRAWINGS

FIG. 3 shows a slower onset with a prolonged duration at the substantially zero-order delivery as evidenced by the results from an in vitro flux study. The tablet dosage from FIGS. 1 and 2 are again included for reference purposes.

DETAILED DESCRIPTION OF THE PREFERRED EMBODIMENTS

Figure 1:
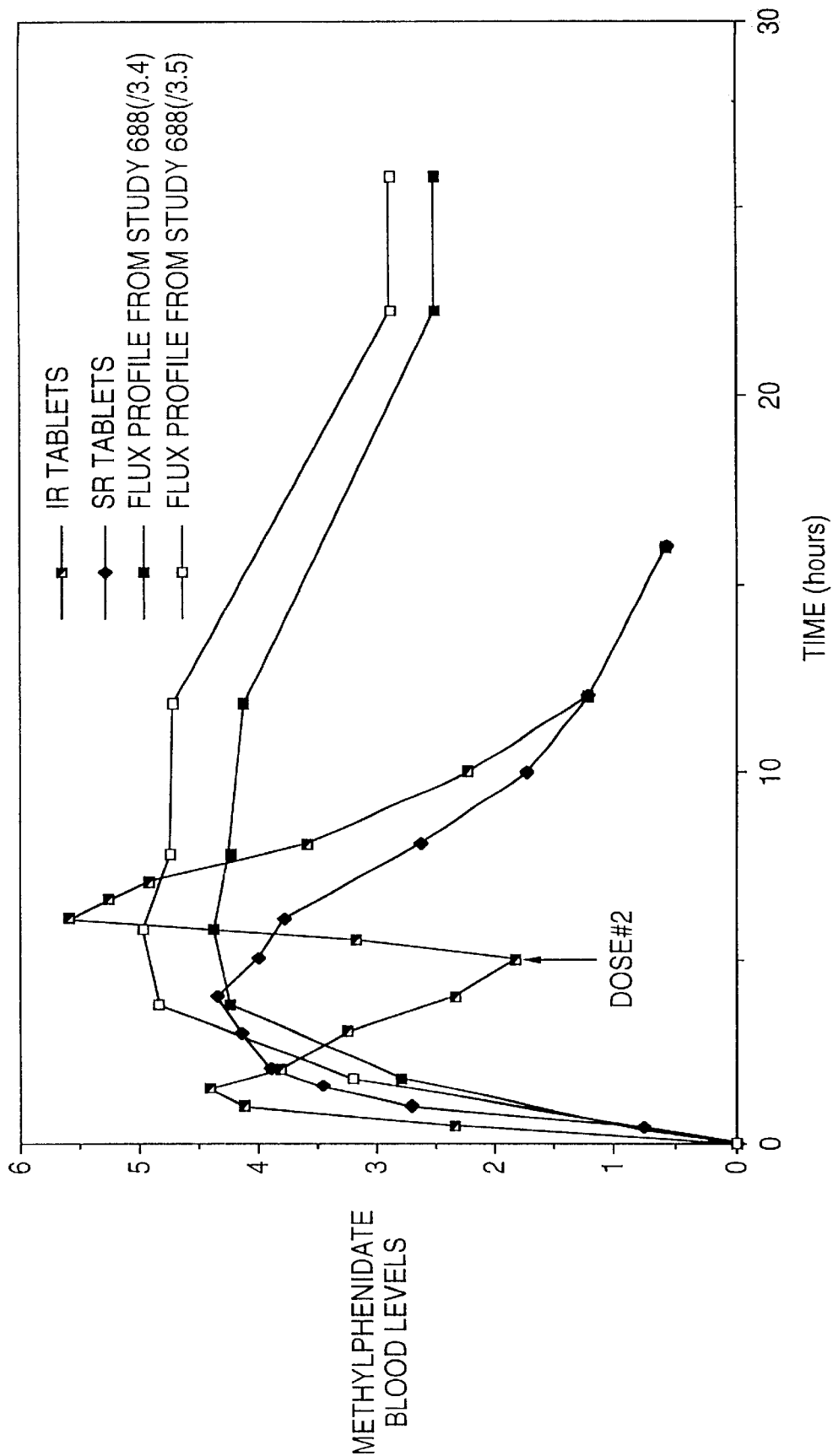
FIG. 1 shows the published blood levels for methylphenidate over time in (a) two doses of the immediate release 10 mg tablets given 5 hours apart, (b) a single dose of the sustained release tablet and (c) the superimposed results from an in vitro flux study. The graph demonstrates the extended duration of the substantially zero-order delivery from the transdermal system.

Methylphenidate has the following general formula:

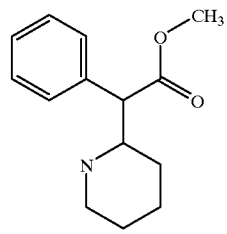

There are four enantiomers which are the (2R:2'R)-(+)-threoenantiomer, the (2S:2'S)-(−)-threo-enantiomer, the (2R:2'S)-(+)-erythro-enantiomer, and the (2S:2'R)-(−)-erythro-enantiomer, but only the d-threo-methylphenidate is significantly active. Commercially available Ritalin is 50:50 d-threo-methylphenidate:1-threo-methylphenidate. The degradation products or metabolites of methylphenidate are also essentially inactive.

Equivalent to the base methylphenidate for the purpose of this invention are the pharmaceutically acceptable acid addition and quaternary salts of the base methylphenidate. Particularly suitable are salts of weak acids. A variety of inorganic and organic acids form pharmaceutically acceptable salts of methylphenidate. The salts are formed with acids such as sulfuric, phosphoric, hydrochloric, hydrobromic, hydriodic, sulfamic, citric, lactic, maleic, malic, succinic, tartaric, cinnamic, acetic, benzoic, gluconic, ascorbic, and related acids. It is also possible to form quaternary ammonium salts with a variety of organic esters of sulfuric, hydrohalic, and aromatic sulfonic acids. Among such esters are methyl chloride and bromide, ethyl chloride, propyl chloride, butyl chloride, isobutyl chloride, benzylchloride and bromide, phenethyl bromide, naphthymethyl chloride, dimethyl sulfate, methyl benzenesulfonate, ethyl toluenesulfonate, ethylene chlorohydrin, propylene chlorobydrin, allyl bromide, methylallyl bromide and crotyl bromide.

The topical compositions contemplated for administration of methylphenidate in accordance with the present invention are in a flexible, finite system.

The term "adhesive" as used herein is intended in its broadest to mean a natural or synthetic polymer that is capable of sticking to the site of topical application, and includes bioadhesives (also referred to a mucoadhesives) and pressuresensitive adhesives as are generally known in the art. A polymer is a adhesive within the meaning of the term is it has the properties of an adhesive per se or if it functions as an adhesive by the addition of tackifiers, plasticizers, crosslinking agents or other additives. Especially preferred adhesives are acrylics, natural and synthetic rubbers, natural and synthetic gums, polysiloxanes, polyacrylates, polyvinylpyrrolidones, vinylpyrrolidone copolymers, styrene block copolymers, and mixtures thereof. Particularly suitable bioadhesives or mucoadhesives include natural or synthetic polysaccharides and polyacrylic acid polymers, and mixtures thereof. The term "polysaccharide" as used herein means a carbohydrate decomposable by hydrolysis into two or more molecules of monosaccharide or their derivatives. Preferred polysaccharides include cellulose materials and natural gums. Such adhesives may be used singularly, or in blends of two or more, or in combination (i.e., in layers).

It has been discovered that methylphenidate, and in particular the base form, can be unstable and undergoes degradation in the presence of acid functional groups which are contained in adhesives, enhancers, excipients and other components of the topical composition. The major degradant/metabolite appears to be ritalinic acid, which increases about ten fold with every 1% increase by weight in such acid functional component. Such degradation can greatly reduce the amount of the active enantiomer during storage of the topical composition, thus reducing the amount of active methylphenidate available for drug delivery.

In view of the foregoing, acrylic polymers that are non-functional, hydroxy functional, or minimally acid functional are preferred. A "minimally acid functional acrylic" is defined as an acrylic polymer having no more than about 5 wt % of acid functional monomers, preferably no more than about 1 wt %, and more preferably no more than about 0.6 wt % of acid functional monomer, based on the weight of the acrylic polymer.

Further instability, in terms of a yellowing color change which may be undesirable in a finished product, has been observed in the presence of vinyl acetate. Thus, while vinyl acetate and adhesives containing vinyl acetate monomer units, such as ethylene/vinyl acetate copolymers, and vinyl pyrrolidone/vinylacetates, have been found to satisfactorily work, the use of these is generally not as preferred as the other adhesives listed above.

It has further been discovered that use of capped (or amine-compatible) polysiloxanes also increase stability and reduce degradation in topical compositions. In addition to reducing the amount of the ritalinic acid, it appears that such polysiloxane polymers reduce the overall reactivity of the composition and therefore the appearance of other degradation products such as the erythro-enantiomers. A "capped" polysiloxane polymer is one which has been chemically treated to reduce or eliminate the silicone-bonded hydroxyl content preferably by substitution with a hydrocarbon radical such as a methyl group. Illustrative examples of capped polysiloxanes include those described in U.S. Pat. No. Re. 35,474, incorporated herein by reference, and which are commercially available from Dow Corning Corporation under their Bio-PSA X7-4100, -4200 and -4300 product series.

The phrase "flexible, finite system" is intended to mean solid form capable of conforming to the surface with which it comes into contact, and which is capable of maintaining the contact in such solid form so as to facilitate topical application without adverse physiological response, and without being appreciably decomposed by aqueous contact during administration to a patient.

Illustrative examples of suitable adhesives and flexible, finite delivery systems include those described in U.S. Pat. Nos. 5,474,783, and 5,656,386 both assigned to Noven Pharmaceuticals, Inc., Miami, Fla. (incorporated herein by reference).

Other flexible, finite systems known in the art include films, plasters, dressings, and bandages, as well as multi-layer delivery systems in which the drug is solubilized or contained in one or more separate layers and reservoir-type delivery systems in which the drug is solubilized or contained in a reservoir or depot separate form the adhesive which attaches directly to the skin or mucosa.

In addition, the solubility of the methylphenidate can be altered by the optional addition of an agent which increases the solubility of methylphenidate in the topical application system, such as polyvinylpyrrolidone.

Of course the composition according to the present invention can also contain agents known to accelerate the delivery of a drug through the skin. These agents have been referred to as skin-penetration enhancers, accelerants, adjuvants, and sorption promoters, and are herein referred to collectively as "enhancers." This class of agents includes those with diverse mechanisms of action including those which have the function of improving the solubility and diffusibility of a drug within the multiple polymer and those which improve percutaneous adsorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of a drug.

Some examples of enhancers are polyhydric alcohols such as dipropylene glycol, propylene glycol, and polyethylene glycol which enhance drug solubility; oils such as olive oil, squalene, and lanolin; fatty ethers such as cetyl ether and oleyl ether; fatty acid esters such as isopropyl myristate which enhance drug diffusibility; urea and urea derivatives such as allantoin which affect the ability of keratin to retain moisture; polar solvents such as dimethyldecylphosphoxide, methyloctylaulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

Prior to the present composition and method of treatment of AD, methylphenidate was administered in a dosage form (immediate release tablets or sustained release tablets) which did not consider the need for a "sleep window" in patients early on in treatment. There is a time frame referred to as a "sleep window", which begins about 30 minutes prior to the end of the efficacy period for the preceding dose and extends from about 30 to 60 minutes beyond the end of the efficacy period for that dose. This gives a 60 to 90 minute period of time when the patient can lie down and drift into restful sleep. If the delay is longer, the rebound symptoms may be fully present, which then prevents a person from going to sleep. The result is an apparent overstimulation insomnia that is not related to too much medication, but to a drop in blood level of the medication. Rebounding is a return of the AD symptoms after the medication wears off. During this period of rebounding, the symptoms of AD may actually be worse than they were before dosing.

According to the present invention, the inventors have found that methylphenidate may be administered to the human body via topical application delivery for the purpose of treating AD if administered in an amount effective to achieve substantially zero-order kinetics for the period of time of the waking hours of the patient. The present composition would provide a steady release of methylphenidate to the patient via topical application route. A delivery rate of about 0.5 mg/24 hours to about 100 mg/24 hours of methylphenidate, and more preferably from about 2.5 mg/24 hours to about 20 mg/24 hours, is needed to achieve a therapeutically effective dose in a patient. The administration of methylphenidate orally is 20–60 mg per day. The topical application system may contain between about 20–180 mg of methylphenidate or an effective amount which will not crystallize in the system. The amount of methylphenidate in the topical application system can be effective to deliver at least 60 mg of the drug to the patient. The size of the delivery patch would be in the range of from about 2 cm2 to about 60 cm2. The preferred system of this invention delivers about 5 mg per 24 hours and contains about 26.4 mg of methylphenidate base per 10 cm2.

As used herein, the term, "flux" is defined as the absorption of the drug through the skin or mucosa, and is described by Fick's first law of diffusion:

$$J = -D(dCm/dx),$$

where J is the flux in g/cm2/sec, D is the diffusion coefficient of the drug through the skin or mucosa in cm2/sec and Dcm/dx is the concentration gradient of the drug across the skin or mucosa.

The inventors have found that there is a relatively wide range of permeability of normal human skin to methylphenidate and this permeability not only varies from individual to individual and site to site, but also is dependent upon the chemical form of the drug. It is preferred that the methylphenidate in the topical application system be in the base form or a base/basic salt combination, or an ester.

As used herein, the term "therapeutically effective dose" intends that dose of methylphenidate that achieves a therapeutic effect, and is typically in the range of about 0.05 mg/kg to about 1.0 mg/kg/day for both children and adults, and more preferably of about 0.075 mg/kg/day to about 0.3 mg/kg/day.

Attainment of substantially of zero-order delivery for at least 10 hours is ensured by providing enough methylphenidate in the topical composition so as to deliver 15 to 40% of the drug in the first 10 hours. Via diffusion kinetics modeling, it can be shown that at depletion rates lower that 20 to 25% from the composition, the kinetics, although truly first order, are substantially zero-order in that they do not significantly deviate from zero-order model at this depletion stage.

A preferred embodiment for attaining at least 10 hours of substantially zero-order delivery is to include in the composition the polymers described above, such as the acrylics having no or minimal functional groups, or the capped silicone polymers. Use of such polymers assists in allowing sufficient amounts of methylphenidate to be loaded into the composition, while preserving the methylphenidate in the active form needed for at least 10 hours of substantially zero-order delivery.

Our invention contemplates the delivery of methylphenidate in therapeutic amounts for continuous periods in topical application systems which rely primarily on skin or mucosa permeability to control drug input rate. It is also contemplated that delivery of the drug can be from a rate controlled system in which the system itself controls the maximum rate at which the drug is delivered through the skin or mucosa.

The phrase, "substantially zero-order" as used herein means delivery of methylphenidate through the skin or mucosa at a rate which is approximately constant once steady state is attained. Typical variability contemplated within the scope of this meaning is about a 30% to about 40% difference from the mean in the blood levels of methylphenidate at steady state (3–10 hours after administration).

EXAMPLES

The following specific examples are included as illustrative of topical application systems and compositions within the contemplation of the invention. These examples are in no way intended to be limiting of the scope of the invention. The weights percentages in the examples are based on dry weight of the system, unless other noted.

The following commercially available adhesives were used in the examples: "Duro-Tak 87-4194, 87-2510, and 87-2097" are trademarks of NATIONAL STARCH AND CHEMICAL CORPORATION, Bridgewater, N.J. for polyacrylate adhesives in organic solutions.

"Bio-PSA X7-4602, X7-4102, X7-4403, X7-4201, X7-4402 and Q7-4502" are trademarks of DOW CORNING CORPORATION, MEDICAL PRODUCTS, Midland, Mich. for polysiloxane adhesives in organic solutions.

"Gelva-Multipolymer Solution (GMS) 1151 and 7882" are trademarks of the Monsanto Company, Saint Louis, Mo. for polyacrylate adhesives in organic solution.

"KOLLIDON 12, 17, 30, 90, and VA 64" are trademarks of BASF Aktiengesellschaft, Ludwigschaften, Germany for polyvinylpyrrolidone polymers and the vinyl acetate/vinylpyrrolidone copolymer.

Methylphenidate is a central nervous system stimulant and is currently sold as Ritalin®, and Centedrin®, by Novartis Pharmaceuticals Corporation.

Example 1

The topical delivery composition was prepared as follows: A mixture of 60 parts of a silicone adhesive (30 parts Bio-PSA X7-4602 and 30 parts Bio-PSA Q7-4502), 20 parts of an acrylic adhesive (Duro-Tak 87-4194) and 20 parts of methylphenidate are added, the mixture in a vessel is agitated until a homogenous mixture is formed. The mixture is then coated on a release liner, the unit is then passed through an oven in order to drive off the volatile solvents. Upon completion of this step, the adhesive-drug component layer is joined to a backing material and the unit is wound into rolls for storage.

Methylphenidate flux through cadaver skin in vitro from the above formulation shows a skin permeability of 5 $\mu$g/cm2/hr to 40 $\mu$g/cm2/hr.

Example 2

(Study 688 (\3.4))

A composition was prepared from 30 Wt % methylphenidate base, 40 wt % Duro-Tak 87-2296 and 30 wt % Bio-PSA X7-4403. The flux profile is shown in FIG. 1.

Example 3

(Study 688 (\3.5))

A composition was prepared from 20 Wt % methylphenidate base, 20 wt % Duro-Tak 87-2296 and 56 wt % Bio-PSA X7-4403 and 4 wt % oleyl alcohol. The flux profile is shown in FIG. 1.

Example 4

(Study 697 (Formula 1/7))

Figure 2:
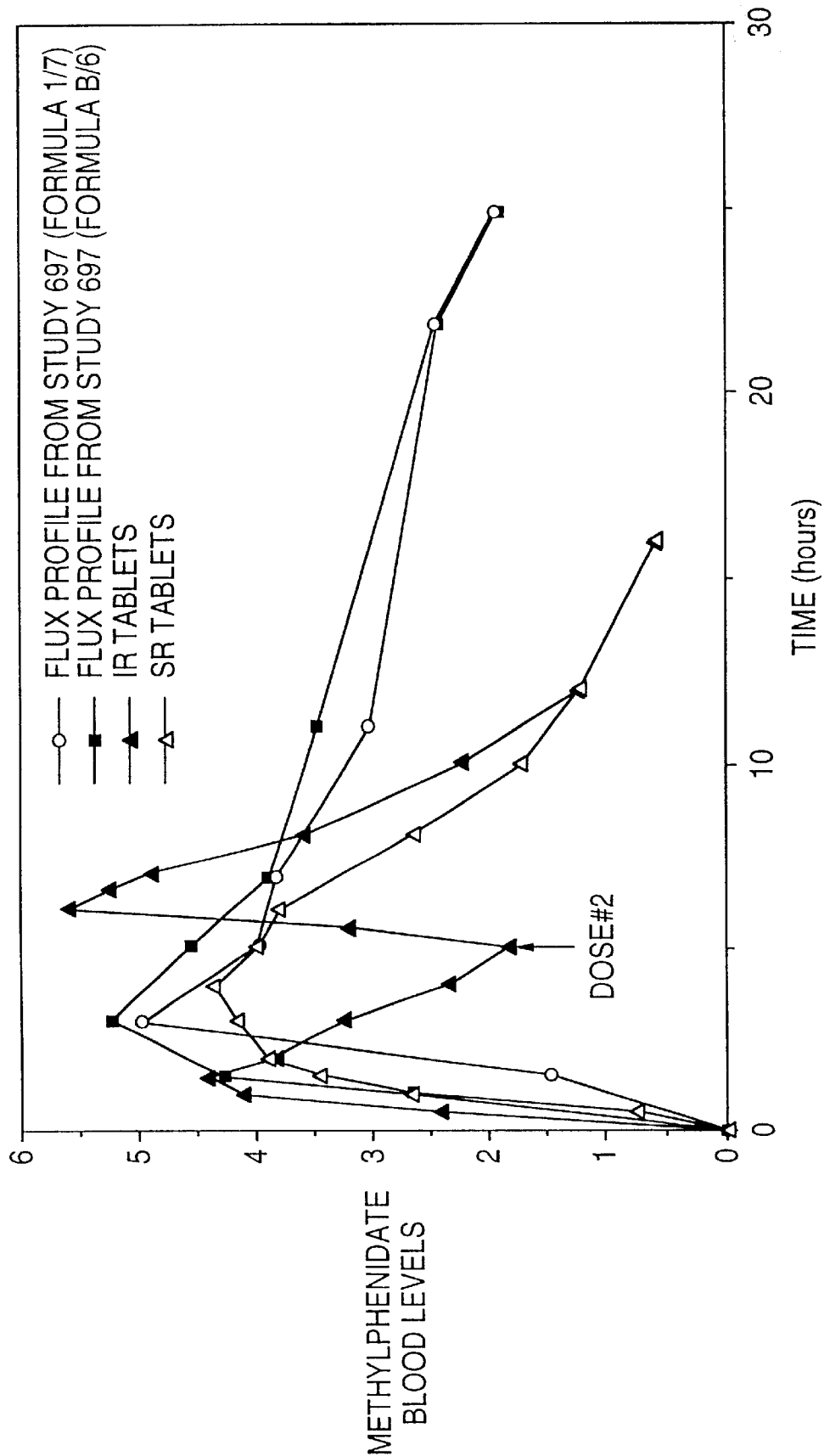
FIG. 2 illustrates the type of delivery kinetics which can result from experimental modifications in the formulation as shown by the results from an in vitro study. As in FIG. 1, the published data for the two doses of the immediate release and the single dose of the sustained releaser tablet have been incorporated as a reference.

A composition was prepared from 20 Wt % methylphenidate base, 40 wt % Duro-Tak 87-2296 and 40 wt % Bio-PSA X7-4403. The flux profile is shown in FIG. 2.

Example 5

(Study 697 (Formula B/6))

A composition was prepared from 20 Wt % methylphenidate base, 20 wt % Duro-Tak 87-2296 and 60 wt % Bio-PSA X7-4403. The flux profile is shown in FIG. 2.

Example 6
(Study 715 (/5))

A composition was prepared from 20 Wt % methylphenidate base, 20 wt % Duro-Tak 87-4194, 30 wt % Bio-PSA X7-4602 and 30 wt % Bio-PSA X7-4502. The flux profile is shown in FIG. 3.

Examples 7–9

| Component (wt % dry) | Example 7 | Example 8 | Example 9 |
|---|---|---|---|
| Acrylic Adhesive (Duro-Tak 87-2510) | 10–20 | 10–20 | 10–20 |
| Polysiloxane Adhesive (Bio-PSA X7-4102) | 60–70 | 0 | 30–35 |
| Polysiloxane Adhesive (Bio-PSA X7-4402) | 0 | 60–70 | 30–35 |
| Methylphenidate base | 20 | 20 | 20 |

| Example (% w/w on a dry basis) | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|
| Bio-PSA X7-4602 (Sillicone adhesive) | 30 | 30 | 30 | — | — | — | — | 30 | — | — | — | — | — | — | — | — | — | — | — | — |
| Bio-PSA Q7-4502 (Silicone adhesive) | 30 | 30 | ☐30 | 60 | 60 | 60 | 60 | 60 | 30 | 70 | 50 | 70 | — | — | — | — | — | — | — | — |
| Duro-Tak 87-4194 (Acrylic adhesive) | 20 | 30 | — | — | 20 | — | — | — | — | — | — | — | 40 | — | — | — | — | — | — | — |
| GMS 1151 (Acrylic adhesive) | — | — | 20 | 20 | — | — | — | — | — | — | — | — | 30 | — | — | — | — | — | — | 40 |
| Duro-Tak 87-2510 (Acrylic Adhesive) | — | — | — | — | — | 20 | — | — | 20 | — | 20 | 25 | — | 70 | 40 | 20 | 30 | — | — | — |
| Duro-Tak 87-2097 (Acrylic adhesive) | — | — | — | — | — | — | 20 | — | — | — | — | — | 10 | 10 | 40 | 60 | 60 | 30 | 30 | 30 |
| GMS 7882 (Acrylic adhesive) | — | — | — | — | — | — | — | 20 | — | — | — | — | — | — | — | — | — | 50 | 60 | 10 |
| Methylphenidate Base (ACTIVE) | 20 | 10 | 20 | 20 | 20 | 20 | 20 | 20 | 20 | 30 | 30 | 5 | 20 | 20 | 20 | 20 | 10 | 20 | 10 | 20 |

Priority U.S. Provisional Application Ser. No. 60/069,510 filed on Dec. 15, 1997, including the specification, abstract, claims and drawings is expressly incorporated by reference in its entirety.

What is claimed is:

1. A composition for topical application of methylphenidate comprising methylphenidate and a pharmaceutically acceptable adhesive carrier in a flexible, finite system,
   wherein the methylphenidate is present in an amount sufficient to achieve substantially zero order kinetics for delivery to the skin or mucosa of a patient in need thereof over a period of time at least 10 hours,
   wherein the proportion of methylphenidate:silicone adhesive:acrylic adhesive (wt % dry) is about 5–30:0–70:0–70, respectively, and
   wherein the composition is substantially free of ritalinic acid at the time of manufacture.

2. The composition according to claim 1, wherein methylphenidate is in the base form.

3. The composition according to claim 2, wherein the methylphenidate base is present within the composition in an amount of at least 26.4 mg per about 10 cm2.

4. The composition according to claim 1, wherein methylphenidate is in the form of a base/basic salt combination or an ester.

5. The composition according to claim 1, wherein the methylphenidate substantially comprises the d-threo-methylphenidate enantiomer.

6. The composition according to claim 1, further comprising an adhesive.

7. The composition according to claim 6, wherein the adhesive is selected from the group consisting of acrylics, natural and synthetic rubbers, bioadhesives, polysiloxanes, polyacrylates, polyvinylpyrrolidones, vinylpyrrolidone copolymers, styrene block polymers and mixtures thereof.

8. The composition according to claim 7, wherein the adhesive includes a bioadhesive which is selected from the group consisting of natural or synthetic polysaccharides and polyacrylic acid polymers.

9. The composition according to claim 8, wherein the natural polysaccharide is a natural gum.

10. The composition according to claim 7, wherein the adhesive includes a polysiloxane which is a capped or amine-compatible polysiloxane polymer.

11. The composition according to claim 7, wherein the adhesive includes an acrylic which is a nonfunctional or minimally functional polymer.

12. The composition according to claim 7, wherein the adhesive includes a polyacrylate which is a non-vinyl acetate containing polymer.

13. The composition according to claim 1, wherein the delivery rate to the skin or mucosa is over a period of time of about 12 to about 20 hours.

14. The composition according to claim 1, wherein the delivery to the skin or mucosa is over a period of time of about 14 to about 16 hours.

15. The composition according to claim 1, wherein the proportion of methylphenidate:silicone adhesive:acrylic adhesive (wt % dry) is 20–30:30–70:10–40, respectively.

16. A composition for topical application of methylphenidate comprising methylphenidate in a flexible, finite system
   wherein the methylphenidate is present in an amount sufficient to permit a delivery rate from about 0.5 mg/24 hours to about 100 mg/24 hours in order to achieve a therapeutically effective dose in a patient,
   wherein the proportion of methylphenidate:silicone adhesive:acrylic adhesive (wt % dry) is about 5–30:0–70:0–70, respectively, and
   wherein the composition is substantially free of ritalinic acid at the time of manufacture.

17. The composition according to claim 16, wherein the delivery rate is from about 2.5 mg/24 hours to about 20 mg/24 hours.

18. The composition according to claim 17, wherein the therapeutically effective dose is from about 0.05 mg/kg/day to about 1.0 mg/kg/day.

19. The composition according to claim 17, wherein the therapeutically effective dose is from about 0.075 mg/kg/day to about 0.3 mg/kg/day.

20. The composition according to claim 16, wherein the therapeutically effective dose is from about 0.05 mg/kg/day to about 1.0 mg/kg/day.

21. The composition according to claim 16, wherein the therapeutically effective dose is from about 0.075 mg/kg/day to about 0.3 mg/kg/day.

22. A composition for transdermal delivery of methylphenidate, comprising methylphenidate or a pharmaceutically acceptable salt thereof in an amount sufficient to provide a flux of at least 5 $\mu g/cm^2/hr$ to achieve therapeutic blood levels of methylphenidate for at least 10 hours.

23. A composition according to claim 22, wherein the methylphenidate is present in a therapeutically effective amount for children.

24. A composition for transdermal delivery of methylphenidate, comprising methylphenidate or a pharmaceutically acceptable salt thereof in an amount to provide a dose of at least 0.5 mg to a patient over 24 hours with a flux of at least 5 $\mu g/cm^2/hr$ for at least 10 hours.

25. A composition for transdermal delivery of methylphenidate, comprising methylphenidate or a pharmaceutically acceptable salt thereof in an amount sufficient to achieve blood levels of methylphenidate in the range of 1 ng/ml to 6 ng/ml for at least 10 hours.

26. The composition of claim 25, wherein said blood levels of methylphenidate are in the range of 1 ng/ml to 6 ng/ml for at least 20 hours.

27. A composition for topical application of methylphenidate comprising methylphenidate and a pharmaceutically acceptable adhesive carrier in a flexible, finite system, wherein the methylphenidate is present in an amount sufficient to achieve substantially zero order kinetics for delivery to the skin or mucosa of a patient in need thereof over a period of time at least 10 hours, wherein the methylphenidate is present at a therapeutically effective amount that is substantially free of crystals, and wherein the composition is substantially free of ritalinic acid at the time of manufacture.

28. A method of treating attention deficit disorder and attention deficit/hyperactivity disorder comprising topically administering methylphenidate in a flexible, finite system wherein the methylphenidate is present in an amount sufficient to achieve substantially zero order kinetics for delivery to the skin or mucosa of a patient in need thereof over a period of time at least 10 hours, wherein the proportion of methylphenidate:silicone adhesive:acrylic adhesive (wt % dry) is about 5–30:0–70:0–70, respectively, and wherein the composition is substantially free of ritalinic acid at the time of manufacture.

29. A method of treating attention defict disorder and attention deficit/hyperactivity disorder comprising topically administering methylphenidate in a flexible, finite system wherein the methylphenidate is present in an amount sufficient to permit a delivery rate from about 0.5 mg/24 hours to about 100 mg/24 hours in order to achieve a therapeutically effective dose in a patient.

30. A method of treating attention deficit disorder (ADD) or attention deficit/hyperactivity disorder (ADHD), comprising transdermal administration of methylphenidate or a pharmaceutically acceptable salt thereof to an individual with ADD or ADHD, at a rate in excess of 5 $\mu g/cm^2/hr$.

31. A method of treating attention deficit disorder (ADD) or attention deficit/hyperactivity disorder (ADHD), comprising transdermal administration of methylphenidate or a pharmaceutically acceptable salt thereof to an individual with ADD or ADHD, at a rate in excess of 0.05 mg/kg/day.

* * * * *

UNITED STATES PATENT AND TRADEMARK OFFICE
Certificate

Patent No. 6,348,211                                                                               Patented: February 19, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David Kanios; Juan Mantelle; Terese A. Dixon, all of Miami, Florida.

Signed and Sealed this Seventeenth Day of December 2002.

JOSE G. DEES
*Supervisory Patent Examiner*
Art Unit 1616

UNITED STATES PATENT AND TRADEMARK OFFICE
CERTIFICATE OF CORRECTION

PATENT NO.   : 6,348,211 B1  Page 1 of 1
DATED        : February 19, 2000
INVENTOR(S)  : Juan Mantelle et al.

It is certified that error appears in the above-identified patent and that said Letters Patent is hereby corrected as shown below:

<u>Title page,</u>
Item [75], Inventors, please delete and insert as follows:

-- [75]  Inventors:  Juan Mantelle; Terese A Dixon; David Kanios, all of Miami, FL. --

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,348,211 B1
APPLICATION NO. : 09/618626
DATED : February 19, 2002
INVENTOR(S) : Juan Mantelle et al.

It is certified that error appears in the above-identified patent and that said Letters Patent is hereby corrected as shown below:

ON THE TITLE PAGE OF THE PATENT

Item (63): Please replace "Continuation of application No. 09/161,351, filed on Sep. 30, 1998, now patent 6,149,374." with -- Continuation of application No. 09/163,351, filed on Sep. 30, now patent 6,210,705. --.

IN THE SPECIFICATION

Column 1, line 7, please replace "The present application is a continuation of U.S. patent application Ser. No. 09/161,351, filed Sept. 30, 1998, now U.S. Pat. No. 6,149,374, which claims the benefit of U.S. provisional application No. 60/069,510, filed Dec. 15, 1997." with -- The present application is a continuation of U.S. patent application Ser. No. 09/163,351, filed Sept. 30, 1998, now U.S. Pat. No. 6,210,705, which claims the benefit of U.S. provisional application No. 60/069,510, filed Dec. 15, 1997 --.

Signed and Sealed this
Tenth Day of May, 2016

Michelle K. Lee
*Director of the United States Patent and Trademark Office*